United States Patent [19]
Katona

[11] Patent Number: 5,689,837
[45] Date of Patent: Nov. 25, 1997

[54] WATER ACTUATED TOILET FAN

[76] Inventor: Thomas J. Katona, 1681 Barnett Cir., Pleasant Hill, Calif. 94523

[21] Appl. No.: 661,886

[22] Filed: Jun. 11, 1996

[51] Int. Cl.$^6$ ................................. E03D 9/03; E03D 9/04
[52] U.S. Cl. ............................ 4/214; 4/226.1; 4/227.1
[58] Field of Search ........................... 4/306, 347, 348, 4/349, 214, 215, 227.1, 223, 224, 226.1, 222, 222.1, 227.2, 227.4

[56] References Cited

U.S. PATENT DOCUMENTS

| | | |
|---|---|---|
| 703,762 | 7/1902 | Carpenter et al. |
| 1,298,171 | 3/1919 | Burdin ............................ 4/214 |
| 2,472,383 | 6/1949 | Owens ............................ 4/222 |
| 2,603,797 | 7/1952 | Baither ............................ 4/214 |
| 3,588,926 | 6/1971 | Buck, Jr. ........................ 4/227.1 |
| 3,605,126 | 9/1971 | Henry ............................. 4/347 |
| 3,824,637 | 7/1974 | Hunnicutt, Jr. ................. 4/213 |
| 3,927,429 | 12/1975 | Pearson ......................... 4/213 |
| 4,011,608 | 3/1977 | Pearson ......................... 4/213 |
| 4,117,559 | 10/1978 | Boyle ............................ 4/209 |
| 4,153,956 | 5/1979 | Fischer, Sr. et al. ........... 4/213 |
| 4,166,298 | 9/1979 | Pearson ......................... 4/213 |
| 4,232,406 | 11/1980 | Beeghly et al. ................ 4/213 |
| 4,852,191 | 8/1989 | Giglio ............................ 4/228 |
| 5,054,130 | 10/1991 | Wilson ........................... 4/213 |
| 5,257,421 | 11/1993 | Rose et al. .................... 4/214 |
| 5,317,762 | 6/1994 | Horst et al. ................... 4/227.1 |

FOREIGN PATENT DOCUMENTS

| | | | |
|---|---|---|---|
| 33594 | 8/1924 | Denmark ......................... 4/214 |
| 227008 | 10/1910 | Germany ........................ 4/214 |
| 2935942 | 3/1981 | Germany ........................ 4/214 |
| 2613 | 3/1899 | United Kingdom ............ 4/214 |

*Primary Examiner*—Henry J. Recla
*Assistant Examiner*—Charles R. Eloshway
*Attorney, Agent, or Firm*—Bielen, Peterson & Lampe

[57] ABSTRACT

A toilet fan assembly inserted between the water shut-off valve and the toilet intake connector that ventilates the area surrounding the toilet and neutralizes odors through automatic activation of a water-driven fan after the toilet is flushed, the toilet fan assembly requiring no modification to existing toilet fixtures and requiring no electrical power source.

11 Claims, 3 Drawing Sheets

WATER ACTUATED TOILET FAN

BACKGROUND OF THE INVENTION

This invention relates generally to a toilet fan assembly capable of ventilating and neutralizing odors in the area surrounding a toilet after the toilet is flushed. Specifically, this invention relates to a water actuated toilet fan inserted between the water shut-off valve and the toilet intake connector that ventilates and neutralizes odors through activation of a water-driven fan automatically after the toilet is flushed.

Since the early 1900's, inventors have attempted to eliminate or mask the odors that arise during the normal use of toilets. Despite the apparent ingenuity of the resulting patented devices, none has attained commercial success. The earliest patented device using water as the driving medium required the user to substantially reconfigure the external plumbing set-up, and its effectiveness relied on an antiquated plumbing system with an overhead reservoir now rarely used.

A second class of inventions is adapted to a modern toilet, but the devices of this class occupy the toilet's interior water tank with a complex system of pipes and valves. Some of these devices also require specialized plumbing connections in the rim, the water basin, or the water tank.

These inventions share two common drawbacks; first, an individual desiring one of these devices would be forced to replace his existing toilet. Second, these devices would be more prone to mechanical breakdown because of the number and complexity of components used. Repairs would likely require professional help and would cost more to fix than repairs for the traditional toilet.

A third class of inventions includes devices that attempt to circumvent a complex pipe and valve assembly by incorporating an electrical motor-driven ventilation system into the toilet design or as a toilet attachment. Some of these devices could not be easily adapted to fit into an existing toilet, again making their use expensive. Others in this class required installation of a vent in the wall adjoining the toilet, making installation expensive. All inventions in this class require an electrical outlet in the vicinity of the toilet, which if available, raises important safety considerations. Some of these devices are designed to operate on the floor nearby the exterior of the toilet bowl or below the water tank, and could easily short-circuit if the toilet were to backup and overflow.

These problems with the prior art are solved by the devised apparatus that is inexpensive, connects easily to an existing toilet, and is powered by the water pressure in the plumbing line.

It is an object of this invention to ventilate and deodorize the area surrounding a toilet in a low-cost, low-maintenance, and safe manner using a device that can easily be added to an existing toilet system.

SUMMARY OF THE INVENTION

The preferred water-actuated, toilet-fan device of this invention is an assembly having three principal members: a deodorizing member, a water-wheel member, and a fan member.

One end of the deodorizing member has a conduit with a threaded connector that is attached to the water shut-off valve, which typically is a metal assembly that protrudes from the wall that is next to the toilet. Pressurized water travels from the water shut-off valve and into the conduit. The conduit terminates with a ball valve assembly that allows the user to shut off the water flow into the deodorizing member.

Water flows through the deodorant housing through a cavity with a receptacle chamber for a deodorant tablet. One side of the deodorant housing has a door to enclose a deodorant tablet contained in the receptacle. To insert or replace a deodorant tablet, the user unlatches the top of a door that forms the outer face of the deodorant housing. The door is hinged along the bottom, allowing the tablet to be inserted at the top.

The inner face of the deodorant tablet receptacle is perforated and allows water traveling through the inner cylindrical pipe to contact the deodorant tablet before the water exits from the deodorant housing. The deodorant tablet slowly dissolves and eventually requires replacement.

The deodorant housing has an exit conduit that terminates with a ball valve assembly that allows the user to shut off the water flowing away from the deodorant housing to prevent back flow when replacing a tablet. The tablet may be a conventional deodorizing and cleaning tablet normally installed within the tank to maintain the toilet clean and fresh smelling.

Water travels away from the deodorizing member through a conduit with a connector that connects the deodorizing member to the water-wheel member. The outer housing of the water-wheel member is cylindrical with side disks forming a chamber. The outer housing of the water-wheel member is sealed so that no water entering the water-wheel member leaks out.

Inside the water-wheel member is a rotor with perimeter-vanes. The axis of the rotor is perpendicular to the direction of the water flow and a shaft located along the axis through the rotor is connected to the two parallel side disks by sealed bearings.

Curved protruding vanes are attached to the outer perimeter of the rotor and are sized in a manner that the vanes do not touch the inner surface of the housing or side disks and the rotor can spin freely. Water enters the bottom of the water-wheel member through an inlet connected to the conduit exiting from the deodorizing member. The water then catches the curved protruding vanes and some of the water's linear motion is transferred to rotary motion about the axis of the rotor.

One end of the rotor shaft terminates at the interface between the bearings and one of the side disks forming a side of the housing. The other end of the shaft extends beyond the other side disk forming a baffle and through an internal compartment and into the fan member. Inside the fan member, a fan with a set of rectangular-shaped blades that are radially attached to a sleeve that is keyed to the shaft.

In the preferred embodiment, the fan blades are impregnated with a deodorant or odor absorbing substance that neutralizes odors in the vicinity of the fan member and circulates the treated air throughout the bathroom. Naturally, the efficacy of the odor abatement will decrease as the apparatus is used, and once spent the user replaces the paddles with a new set.

To prevent injury, a vented shell covers the fan and may comprise a unitary housing structure with the water-wheel member. A grill made of movable slats covers the front face of the vented shell. The movable slats are connected to a lever that positions the slats in unison and allows the user to direct the air leaving the fan to maximize air circulation.

An outflow conduit receives the water as it exits from the water-wheel member and has a connector that connects to the intake receptacle of the water tank of the toilet. The user installs the apparatus by first draining the toilet and closing the water shut-off valve. The user then connects the intake conduit of the assembly into the water shut-off valve, and connects the outflow connector into the intake receptacle of the water tank. The water shut-off valve is opened, and the device is operable.

Once the device is installed, the user operates the toilet exactly as before. The device is activated after the toilet is flushed. Once flushed, the valve connected to the flushing lever opens and allows water to fill the water tank. While the water tank is refilling, water travels from the shut-off valve, through the water-wheel member of the assembly, and into the water tank. The movement of water through the device during the water tank refill causes the rotor to spin and the fan to rotate and displace the air in the vicinity of the toilet. Where desired or when space limitations require, the deodorizing member of the assembly can be eliminated. These and other features will become apparent from a consideration of the Detailed Description of the Preferred Embodiments.

DETAILED DESCRIPTION OF THE PREFERRED EMBODIMENTS

Figure 1:
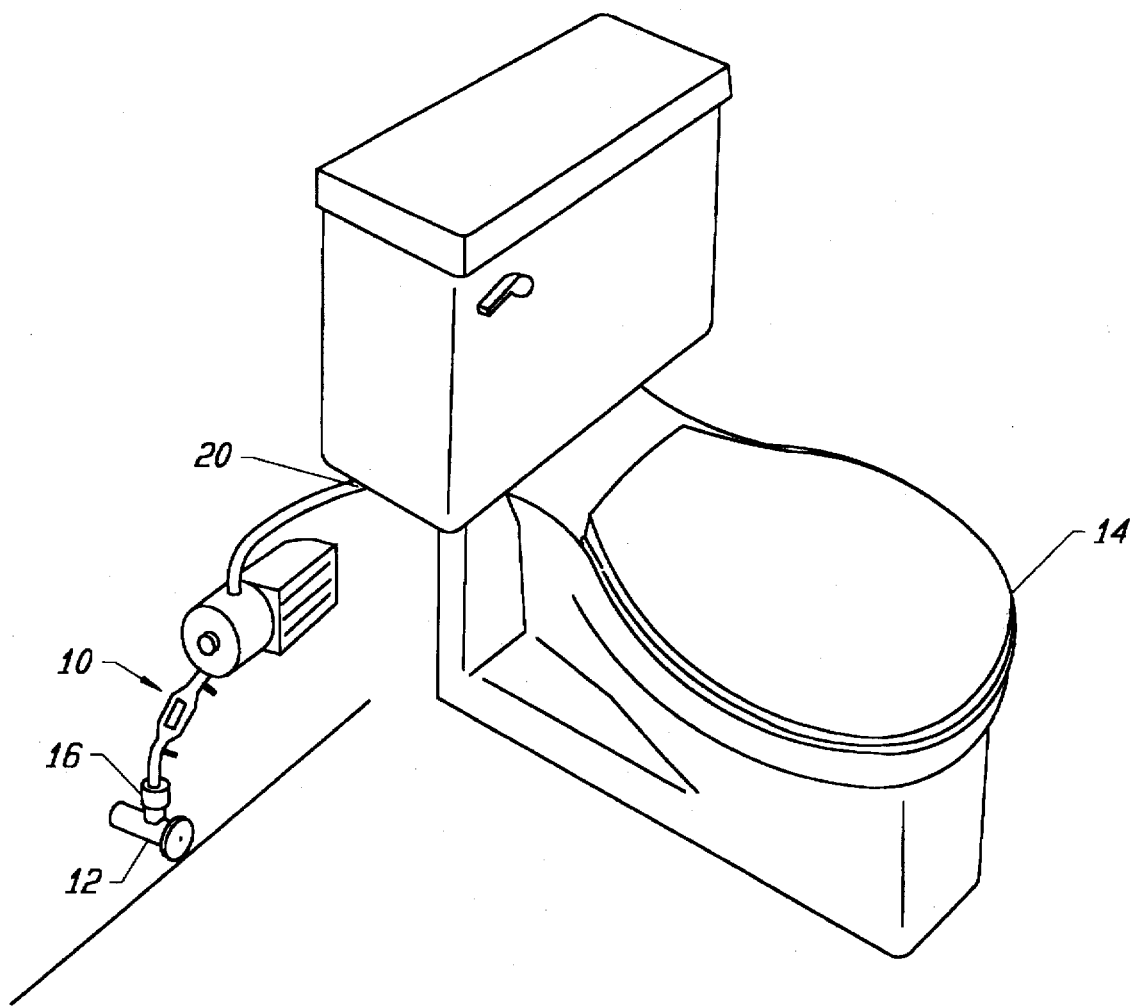
FIG. 1 is a corner perspective view of the water pressure-activated toilet deodorizer device installed on a typical bathroom toilet.

Referring to FIG. 1, the water-actuated toilet fan, designated generally by the reference numeral 10, is shown as an integrated assembly attached to the plumbing of a conventional toilet 14. A water shut-off valve 12 protrudes from the wall nearby the toilet 14 and water travels through a pipe that terminates with a male screw connector 16. Similarly, the toilet water tank 18 has a male intake connector 20 that serves as the inlet for the water used by the toilet 14. The toilet fan 10 is installed between the screw connector of the shut-off valve 12 and the intake connector 20 of the toilet 14.

The original connection assembly between the male screw connector 16 and the male intake connector 20, usually a hose or pipe, is disconnected. The intake screw connector 22 of the toilet fan 10 is connected to the male screw connector 16. The outflow conduit or outflow connector 24 of the toilet fan 10 is connected to the male intake connector 20 of the toilet 14. The toilet fan 10 is operational when the shut-off valve 12 is turned on.

Figure 2:
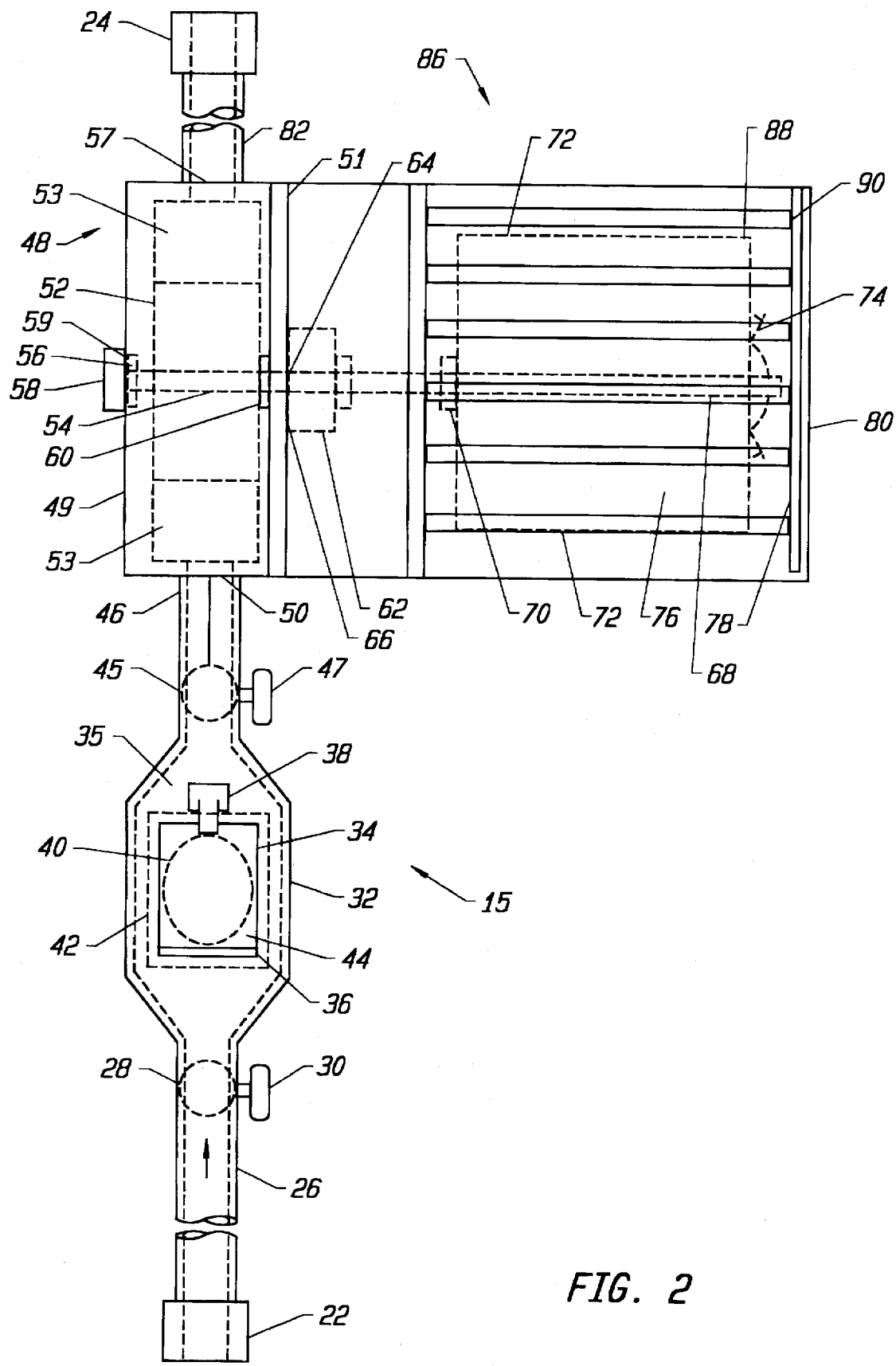
FIG. 2 is a cross sectional view of the device of FIG. 1.
Figure 3:
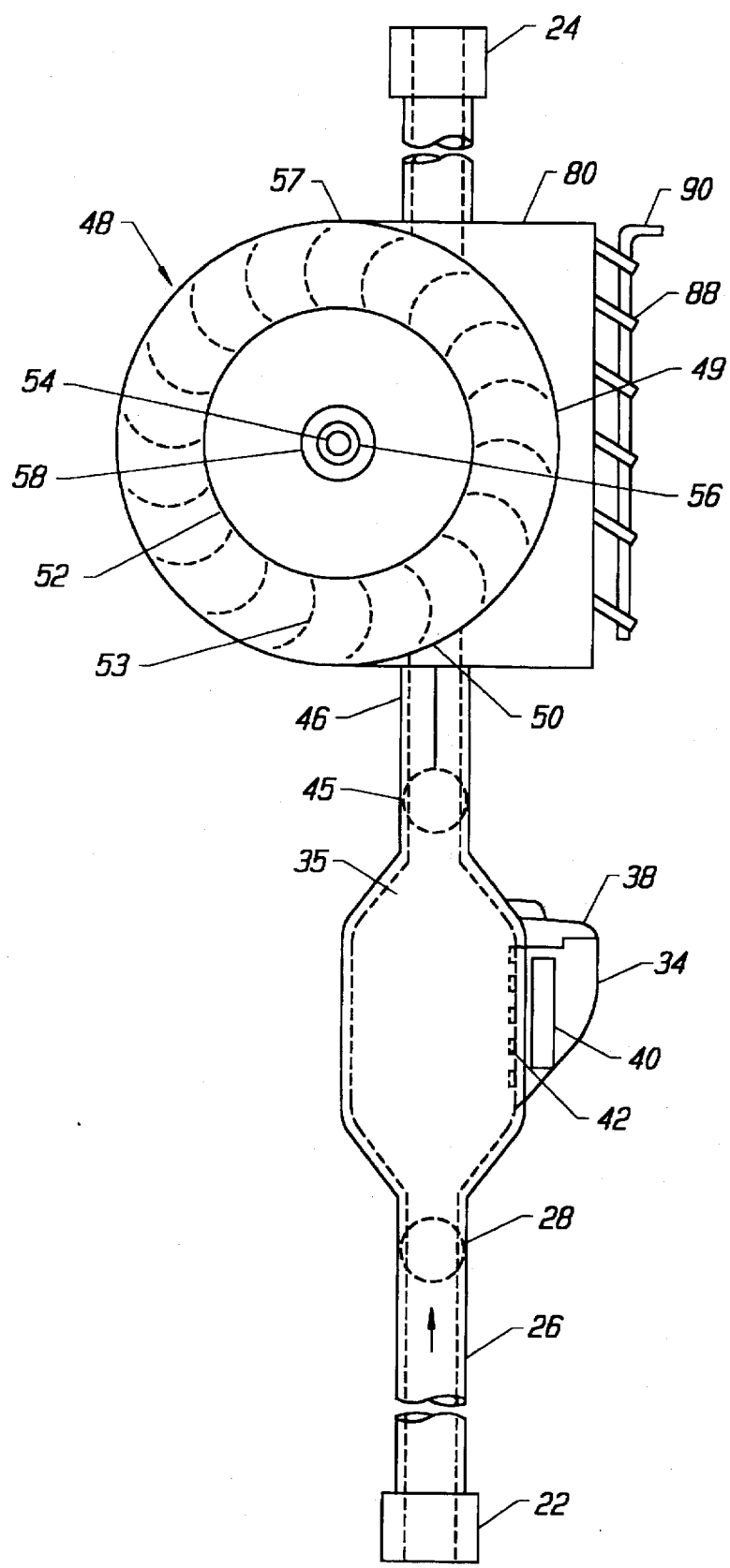
FIG. 3 is a side cut-away view of the deodorizing member and the fan member of the device of FIG. 1.

Referring to FIG. 2, water enters the deodorizing member, designated generally by the numeral 15, through the intake screw connector 22. Connected to the intake screw connector 22 is a conduit, shown as a flexible intake hose 26. Water flow through the deodorizing member 15 is designated by arrows. The other end of the flexible intake hose 26 connects to a lower ball valve 28 and the user controls the amount of water flowing through the flexible intake hose 26 by twisting the lower ball valve switch 30.

Attached to the lower ball valve 28 is the deodorant housing 32 that is typically made of plastic and in the preferred embodiment flares out forming a rectangular enclosure that is wider than the diameter of the flexible intake hose 26. Protruding from the front of the deodorant housing 32 is a door 34 that is connected to the deodorant housing 32 by a hinge 36 at the bottom of the door 34 and secured by a latch 38 above the door 34.

The door 34 encloses a chamber 35 allowing water to continue flowing through the deodorizing member 15. Located inside the deodorant housing 32 is a deodorant tablet 40 (shown in phantom) that is held in place in the chamber 35 and behind the door 34 by a receptacle 44. The deodorant tablet 40 can be inserted or removed once the door 34 is opened by unhooking the latch 38. The receptacle 44 allows water in the chamber 35 to make contact with the deodorant tablet 40. Attached to the inner surface of the deodorant housing 32 located around the perimeter of the door 34 is a seal 42 that prevents water from leaving the deodorizing member 15 through the perimeter of the door 34.

The top of the deodorant housing 32 flares inward and connects to an upper ball valve 45. Water leaving the chamber 35 passes through the upper ball valve 45 and travels upward through a connecting conduit 46. The user controls the rate of water traveling through the connecting conduit 46 by twisting the upper ball valve switch 47.

Water traveling through the connecting conduit 46 enters the bottom of the water-wheel member 48 through an inlet 50. The outer housing of the water-wheel member 48 is cylindrical with an outer side disk 49 and an inner side disk 51 forming a chamber. The water-wheel member 48 contains a rotor 52 that rotates about a rotatable shaft 54 that is fixed to the rotor 52.

Attached to the rotor 52 are perimeter-vanes 53 that project out radially from the rotor 52. Water entering through the inlet 50 catches the perimeter-vanes 53, causing the perimeter-vanes 53, the rotor 52, and the rotatable shaft 54 to rotate about an axis along the rotatable shaft 54. Water then exits the water-wheel member 48 through an outlet 57 that connects to an exit conduit, displayed here as a flexible outflow hose 82. The opposite end of the flexible outflow hose 82 terminates with the outflow screw connector 24.

One end of the rotatable shaft 54 is inserted into the aperture of a sealed bearing member 58 having a stationary rim 59 attached to the outer disk 49. A seal 56 surrounds the perimeter of the rotatable shaft 54 and makes contact with the outer disk 49.

The rotatable shaft 54 passes through an aperture 64 through the inner disk 51 and is surrounded by a seal 60. The rotatable shaft 54 then passes through the aperture of a sealed bearing member 62 whose stationary rim 66 is attached to the outer surface of the inner disk 51.

The rotatable shaft 54 protrudes outward from the inner disk 51 and enters the fan member, designated generally by the numeral 86. Fitted over the end of the rotatable shaft 54 is a thin cylindrical tube 68 having an aperture slightly larger than the diameter of the rotatable shaft 54. One end of the cylindrical tube 68 is held stationary by a stop 70 that is affixed to the rotatable shaft 54 and the cylindrical tube 68 rotates at the same angular frequency as the rotatable shaft 54.

Fan blades 72 are affixed along the length of the cylindrical sleeve 68 and protrude radially from the cylindrical sleeve 68. Connecting the end of the cylindrical sleeve 68 to the rotatable shaft 54 is a spring clip 74. Because the fan blades 72 are held stationary relative to the cylindrical sleeve 68, the fan blades 72 rotate at the same angular frequency of the rotatable shaft 54. In the preferred embodiment the fan blades 72 are coated with or manufactured from a deodorizing material that further aids the odor removal around the toilet 14.

Alternately, or in conjunction with the deodorizing fan blades 72, a filter 76 impregnated with an odor control substance, such as activated charcoal impregnated with an odor masking perfume may be installed in an opening 78 in an outer shell 80.

The vented outer shell 80 is attached to the outer surface of the water-wheel member 48 and encloses the rotatable shaft 54 and fan blades 72. The vented outer shell 80 is vented to allow air to easily circulate about the fan blades 72 and the surrounding environment. In the preferred embodiment, the vented outer shell 80 is square-shaped and the front face of the outer vented shell 80 at the opening 78 has synchronized movable slat members 88 that the user adjusts with lever 90 to direct the air flow leaving the fan blades 72.

While, in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. In a conventional tank-type toilet having a toilet bowl, a tank, and a plumbing system with a water flow connected to the tank, the improvement comprising a water-actuated toilet fan connected to the plumbing system and to the tank, for the recirculation of the air, in the vicinity of the toilet exteriorly thereto, the toilet fan including:

a housing external to the toilet having a water compartment and an air compartment;

intake means connected to the plumbing system and to the water compartment of the housing for intake of the water flow for the toilet from the plumbing system;

rotation means in the water compartment for transferring energy from the water flow through the water compartment into rotational motion;

air recirculation means in the air compartment connected to the rotational means for transferring the rotational motion from the rotation means to an air flow, wherein the air compartment, is vented and has an opening for air flow leaving the air compartment the toilet fan including deodorization means for deodorizing air flow leaving the air compartment of the toilet fan; and outflow connection means connected to the water compartment of the housing for directing the water flow out of the toilet fan and into the tank.

2. The toilet fan of claim 1 with chemical tablet means for deodorizing and cleaning water in the toilet, the housing having compartment means for placing of a chemical in tablet form therein that makes contact with the water flow through the toilet fan.

3. The toilet fan of claim 2 wherein the means for placing a chemical in tablet form includes means for the replacement of the tablet.

4. The toilet fan of claim 1 wherein the deodorization means comprises a filter in the opening of the air compartment of the housing for the deodorization of the air around the toilet, the filter having an odor control substance.

5. The toilet fan of claim 1 wherein the air recirculation means comprises fan blades and the deodorization means comprises a deodorizing material on the fan blades.

6. In a conventional tank-type toilet having a toilet bowl, a tank, and a plumbing system with a water flow connected to the tank, the improvement comprising:

a water-actuated toilet fan connected to the plumbing system and the toilet, for the recirculation of the air in the vicinity of the toilet exteriorly thereto, the toilet fan including:

a housing external to the toilet having a water compartment and an air compartment;

a water-wheel in the water compartment with an axis of rotation that transfers energy from the water flow through the water compartment into rotational motion;

a shaft attached to the water wheel along the axis of rotation of the water-wheel that rotates at the same frequency as the water-wheel, the shaft extending from the water compartment into the air compartment;

a fan in the air compartment attached to the shaft that rotates at the same frequency as the shaft, wherein an air flow is generated by the rotating fan;

air deodorization means in the air compartment for deodorizing air flow from the air compartment; and an outflow connector on the housing at the water compartment connecting the housing to the toilet tank, wherein the water flow through the water compartment is directed into the toilet tank through the outflow connector.

7. The toilet fan of claim 6 wherein the housing includes a water deodorizer compartment, the deodorizer compartment containing a receptacle for the placement of a deodorizing and cleaning chemical in tablet form therein that makes contact with the water flow through the toilet fan.

8. The toilet fan of claim 7 wherein the receptacle includes means for replacing the deodorizing and cleaning chemical.

9. The toilet fan of claim 8 wherein the fan is impregnated with an air deodorizer.

10. The toilet fan of claim 9 wherein the fan is affixed to the rotatable shaft by a spring clip, the spring clip allowing for the detachment and replacement of the fan.

11. The toilet toilet fan of claim 6 wherein the air compartment is vented and has an opening, the air deodorization means comprising a filter in the opening of the air compartment, the filter having an air deodorizing substance.

* * * * *